United States Patent [19]

Banks et al.

[11] Patent Number: 4,489,083

[45] Date of Patent: Dec. 18, 1984

[54] PHENYL IMIDAZOLE DERIVATIVES

[75] Inventors: Bernard J. Banks, Broadstairs; Alexander B. Penrose, North Deal, both of England

[73] Assignee: Pfizer Inc., New York, N.Y.

[21] Appl. No.: 442,685

[22] Filed: Nov. 18, 1982

[30] Foreign Application Priority Data

Nov. 25, 1981 [GB] United Kingdom ............... 8135453

[51] Int. Cl.³ .................... C07D 513/04; A01N 43/90
[52] U.S. Cl. .................................... 424/270; 548/154
[58] Field of Search ....................... 548/154; 424/270

[56] References Cited

U.S. PATENT DOCUMENTS 3,899,583  8/1975  Spicer et al. ........................ 424/270

FOREIGN PATENT DOCUMENTS 2359804  6/1974  Fed. Rep. of Germany ...... 548/154
1180202  2/1970  United Kingdom .
1293741  10/1972  United Kingdom .
1404708  9/1975  United Kingdom .

*Primary Examiner*—Robert Gerstl
*Attorney, Agent, or Firm*—Charles J. Knuth; Peter C. Richardson

[57] ABSTRACT

A series of bicyclic imidazole and imidazoline derivatives, including their non-toxic acid addition salts, are disclosed. These particular compounds are useful for combatting ectoparasite and helminth infestations in animals, especially sheep and cattle. 2-(2,3-Dimethylphenyl)-2,3,5,6-tetrahydroimidazo[2,1-b]thiazole represents a typical and preferred member compound. Methods for preparing all these compounds from known starting materials are provided.

14 Claims, No Drawings

PHENYL IMIDAZOLE DERIVATIVES

BACKGROUND OF THE INVENTION

This invention relates to a series of bicyclic imidazole or imidazoline derivatives having ectoparasiticidal, especially insecticidal (particularly against blowfly larvae) and acaricidal (including miticidal), and anthelmintic activity.

Eggs are laid by the adult female insects on animal skins, and the larvae produced tend to burrow into the skins of the afflicted animals and thereby spoil the state of the skins, with the consequence, for example, that cattle hides and sheep skins and fleece intended for the manufacture of leather, sheepskin and woollen goods, respectively, are reduced in quality. Furthermore, the state of health and quality of the flesh of afflicted animals may be detrimentally affected. Certain insect larvae, for example, the larvae of blowflies which tend to live in sheep skin, are capable of bringing premature death to the animal if present in sufficient abundance.

British Patent Specification No. 1,404,708 to Rhone-Poulenc S. A. discloses some of the compounds of the present invention, as hereinafter described in formula (I), but only as psychic energizers and antidepressants having anorexigenic properties. In detail, this specification discloses compounds of the formula:

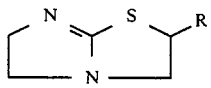

where R represents a phenyl radical unsubstituted or substituted by 1 or 2 atoms or radicals, which—when 2 substituents are present—may be the same or different, selected from halogen atoms and alkyl, alkoxy, alkylthio, dialkylamino, dialkylsulphamoyl, nitro, cyano and trifluoromethyl radicals, or R represents a 2-, 3- or 4-pyridyl radical unsubstituted or substituted by an alkyl or alkoxy radical, the alkyl containing radicals and alkyl moieties of the other radicals containing 1 to 4 carbon atoms, and acid addition salts thereof. The specification states that the compounds of outstanding interest are those wherein R is a phenyl radical or a phenyl radical substituted, preferably in the 3-position, by a halogen atom or an alkyl (preferably methyl) radical, an alkoxy (preferably methoxy) radical, an alkylthio (preferably methylthio) radical, or a nitro or trifluoromethyl radical, and acid addition salts thereof. In all the specific Examples to compounds where R is substituted phenyl, there is either a single substituent in the 3- or 4-position, or, in the case of Example 5, there are 2 substituents, namely chloro in the 3- and 5-positions.

This reference contains no reference to, nor any specific Examples to, compounds where R is a phenyl radical substituted in the 2-position. On the other hand, we have found that compounds of the formula (I), as hereinafter described, in which the benzene ring contains a substituent in the 2-position and optionally, a further substituent or substituents, are especially useful as insecticides, acaricides and anthelmintics and are the preferred compounds of the formula (I) as hereinafter described for this purpose.

In addition, British Patent Specification No. 1,180,202 (Rhone-Poulenc S. A.) discloses compounds of the formula:

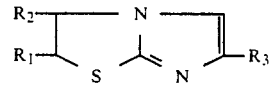

where $R_1$ is hydrogen or phenyl, $R_2$ is hydrogen or methyl and $R_3$ is hydrogen, phenyl or hydroxyphenyl, and their acid addition salts, but only as anti-viral agents.

SUMMARY OF THE INVENTION

Thus, according to the present invention, there is now provided for the first time a method of combatting ectoparasite and helminth infestations in an animal, which comprises administering to said animal an ectoparasiticidal-anthelmintic effective amount of a compound selected from the group consisting of bicyclic imidazole or imidazoline bases of the formula:

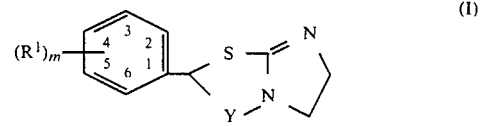

(I)

and the non-toxic acid addition salts thereof, wherein $(R^1)_m$ represents up to four optional substituents, m being zero or an integer of from 1 to 4, and each $R^1$ is independently selected from the group consisting of $C_1$-$C_4$ alkyl, $C_1$-$C_4$ alkoxy, $C_1$-$C_4$ alkylthio, halogen, trifluoromethyl, nitro, cyano, phenyl, phenoxy, —$NH_2$, —$NHCOCH_3$, —OH, —$CH_2OH$, —$CH_2OCH_3$, —CHO, —COOH, —COO($C_1$-$C_4$ alkyl), —$CONH_2$ and —$SO_2N(C_1$-$C_4$ alkyl)$_2$; or $R^1$ and $R^1$, when taken together, represent a —CH=CH—CH=CH—, —$(CH_2)_3$— or $(CH_2)_4$— group attached to adjacent positions of the benzene ring; and Y is —$(CH_2)_2$— or —$CHR^2$—, with $R^2$ being hydrogen or methyl; and the dashed line represents an optional bond. These compounds possess the ability to be particularly effective against blowfly larvae and, in addition, also have activity against the adult and larval stages of nuisance flies which can cause severe distress to cattle. The compounds are also effective as acaricides with good expellency properties, particularly against cattle ticks, and are miticides, e.g., against *Dermanyssus gallinae* (poultry red mite) and *Psoroptes cuniculi* (rabbit ear mite). In addition, the compounds also have excellent anthelmintic activity, e.g., against *Caenorhabditis elegans*.

The compounds of the present invention which are novel per se are those of the formula:

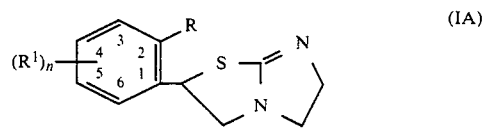

(IA)

and the non-toxic acid addition salts thereof, wherein $(R^1)_n$ represents up to three optional substituents, n being zero or an integer of from 1 to 3, and R and $R^1$, which may be the same or different, are each independently selected from the group consisting of $C_1$-$C_4$ alkyl, $C_1$-$C_4$ alkoxy, $C_1$-$C_4$ alkylthio, halogen, trifluoromethyl, cyano, —$NH_2$, —$NHCOCH_3$, —OH, —$CH_2OH$, —$CH_2OCH_3$, —CHO, —COOH, —COO($C_1$-$C_4$ alkyl), —CONH₂ and —SO₂N(C₁–C₄ alkyl)₂; or R and R¹, when taken together, represent a —CH=CH—CH=CH—, —(CH₂)₃— or —(CH₂)₄— group linking the 2- and 3-positions of the benzene ring.

"Halogen" as used throughout this specification simply means fluorine, chlorine, bromine and iodine. Alkyl, alkoxy, alkylthio and alkylsulfonyl groups of 3 or 4 carbon atoms can be straight or branched chain.

The preferred compounds of the formula (IA) are those wherein (R¹)ₙ is located at the 3- or 6-position of the benzene ring and n is 1. The most preferred compounds of the formula (IA) are those wherein (a) R and R¹ are each methyl; (b) R is methyl and R¹ is halogen or trifluoromethyl at the 3-position; and (c) R is halogen or trifluoromethyl and R¹ is methyl at the 3-position of the benzene ring. Of these, typical representatives include such preferred member compounds as 2-(2,3-dimethylphenyl)-2,3,5,6-tetrahydroimidazo[2,1-b]thiazole, 2-(2,6-dimethylphenyl)-2,3,5,6-tetrahydroimidazo[2,1-b]thiazole, 2-(2-methyl-3-chlorophenyl)-2,3,5,6-tetrahydroimidazo[2,1-b]thiazole, 2-(2-methyl-3-bromophenyl)-2,3,5,6-tetrahydroimidazo[2,1-b]thiazole, 2-(2methyl-3-trifluoromethylphenyl)-2,3,5,6-tetrahydroimidazo[2,1-b]thiazole, 2-(2-chloro-3-methylphenyl)-2,3,5,6-tetrahydroimidazo[2,1-b]thiazole, 2-(2-bromo-3-methylphenyl)-2,3,5,6-tetrahydroimidazo[2,1-b]thiazole, 2-(2-iodo-3-methylphenyl)-2,3,5,6-tetrahydroimidazo[2,1-b]thiazole and 2-(2-trifluoromethyl-3-methylphenyl)-2,3,5,6-tetrahydroimidazo[2,1-b]thiazole.

The compounds of the invention containing one or more asymmetric centres will exist as one or more pairs of enantiomers, and such pairs or individual isomers are separable conventionally. The invention includes the separated and racemic forms.

The invention also includes ectoparasiticidal and anthelmintic compositions, including concentrates, comprising a compound of the formula (I) or (IA), or a non-toxic acid addition salt thereof, together with a diluent or carrier. Preferably the compositions are in the form of a dust, wettable powder, emulsifiable concentrate, or prolonged-release bolus, or may be in the form of an animal dip or injectable formulation.

DETAILED DESCRIPTION OF THE INVENTION

The compounds of the formula (I) and (IA) when used for treating ectoparasitic infections of animals such as sheep and cattle are suitably administered in the form of dusts, dips, "pour-on" formulations or sprays comprising an aqueous emulsion of an emulsifiable concentrate. The latter may be, for example, a 1–40% (g/100 ml) solution of the compound in a non-toxic organic solvent containing an emulsifying agent, and this may be diluted with water to give a concentration of the compound in the aqueous medium of from 0.01 to 0.5% w/v (g/100 ml), or approximately 100 to 5000 p.p.m. Suitable solvents include toluene, xylene and petroleum oil or an alkylated naphthalene.

The volatile solvents, e.g. toluene and xylene, evaporate after spraying to leave a deposit of the active ingredient. Suitable emulsifiers, which can be cationic, anionic or non-ionic as is well known to those skilled in the art, include ordinary soaps (anionic), lauryl pyridinium chloride (cationic) and polyoxethylene lauryl ethers (non-ionic), the latter being, for example, a reaction product of ethylene oxide (10 moles) with dodecyl alcohol (1 mole). The made-up spray or dip may be an emulsion or suspension.

A dust may be made by mixing the appropriate amount of active ingredient with a diluent or carrier such as talc, clay, calcite, pyrophyllite, diatomaceous earth, walnut shell flour, silica gel, hydrated alumina or calcium silicate to afford a concentration of active ingredient of from about 0.25 to about 4% by weight. As an alternative method of preparation, the diluent or carrier is mixed with a solution of the active ingredient in a volatile organic solvent, e.g. benzene or acetone. The solvent is then removed by evaporation and the mixture ground.

Wettable powders may be made by adding suitable wetting agents and conditioning agents to the dusts. They may suitably contain from about 25% to about 75% w/v of active ingredient.

For the control of nuisance flies breeding in dung, the compounds may be incorporated into animal feed. Thus the invention includes an animal feed including a compound of the formula (I) or (IA).

Administration in the form of prolonged-release boluses or implants is also possible. The compounds can also be given by injection.

The compounds may also be administered in combination with conventional ectoparasitical agents such as organophosphates, carbamates, organochlorines, pyrethroids, formamidines, triazapentadienes, triazinethiones or thioureas.

Larvicidal properties are investigated by maintaining test and control groups of *Lucilia cuprina* (blowfly) larvae in separate test tubes, each containing filter paper partially soaked in calf serum serving as food and plugged with cotton wool. The filter paper in the test tube containing the test larvae is additionally impregnated with the compound under investigation to the extent of a 100 mg/m² deposition. Both test tubes are stored with the top part only in a strong light so as to induce the larvae to stay in the lower part of the tubes in contact with the filter paper through exploitation of their aversion to light. Mortality is noted and recorded as a corrected percentage. The finding of substantial numbers of test larvae on the illuminated plug suggests that the test compound has marked repellant properties.

In addition to percentage effectiveness figures, $LD_{90}$ results can be obtained from dose response measurements using any of the afore-described tests.

To assess acaricidal activity, in one test, five freshly collected, fully engorged *Boophilus microplus* adult female ticks are used for each acaricidal compound. Using a micro-pipette 10 microliters of a solution containing, say, 10 micro-grams of the acaricidal compound in ethanol or acetone, is applied to the dorsal surface of each of the ticks. Clearly higher doses can be applied if desired, using the same volume of solution. The treated ticks are placed in weighed 1"×2" glass vials, weighed and stored at 26° C. and 80%+R.H. in plastic boxes for two weeks. The ticks are then removed from the vials and the vials weighed to give the weight of eggs laid by the ticks. Any inhibition in the egg laying of the treated ticks is calculated as a percentage of the eggs laid by untreated control ticks.

The eggs are returned to the incubator for a further 3 weeks after which time the percentage of eggs hatching is estimated.

The percentage reduction in the anticipated reproduction of the ticks is calculated using the weight of eggs laid and the percentage of eggs hatching.

The test may be repeated using smaller amounts of the acaricidal compound.

In another test, using a pipette 0.5 ml of a solution containing 0.5 mg of the acaricidal compound in ethanol or acetone is spread evenly on to a Whatman No. 1 filter paper 8 cm×6.25 cm (50 sp. c.m.) to give a dosage of 100 mg/m².

The treated paper is allowed to dry at room temperature, folded with the treated surface inside and the two short edges sealed with a crimping machine. The open ended envelope is placed in a 1 lb Kilner jar containing damp cotton wool in a plastic pot and stored in an incubator at 26° C. for 24 hours. 20-50 *Boophilus microplus* larvae, which had hatched 8-14 days previously, are placed in the envelope using a small spatula.

The open end is then crimped to form a sealed packet. The treated paper containing the larvae is returned to the Kilner jar and kept for a further 48 hours in the incubator. 20-50 larvae are placed similarly in an untreated paper envelope to act as controls. At the end of the 48 hour test period the mortality is noted and recorded as a percentage after correction for any mortality among the untreated control ticks.

The test may be repeated using smaller amounts of the acaricidal compounds.

In addition to percentage effectiveness figures, $LD_{90}$ results can be obtained from dose response measurements using any of the afore-described tests.

Activity against *Haemaphysalis longicornus* nymphs may be measured in a similar manner to the above larvae test.

In anthelmintic testing, the compounds are screened against *Caenorhabditis elegans* worms in vitro. The assay is based upon the published work of Simpkin and Coles, *J. Chem. Tech. and Biotechnol.*, 31, 66-69, (1981).

Im mite testing, two species of mites are used. These are *Dermanyssus gallinae* (Acarina, Mesostigmata), the poultry red mite, and *psoroptes cuniculi* (Acarina, Astigmata), the rabbit ear mite. The test procedure, using 30-50 mites, is identical to that described for *Boophilus microplus* larvae above.

The compounds of the formula (I) (including [1A]) can be prepared by the following route:

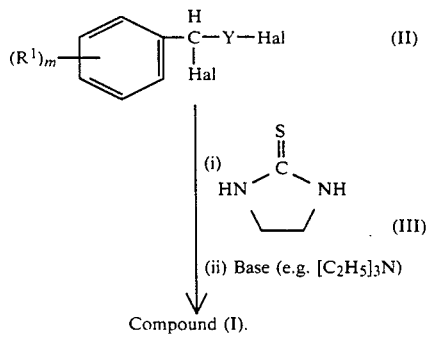

$(R^1)_m$ and Y are as previously defined. "Hal" is Cl, Br, or I. "Hal" is preferably Br.

It is believed that the reaction between compounds (II) and (III) produces th intermediate (IV) set out below, which is then cyclised by the base:

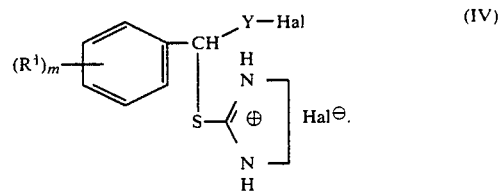

The starting materials (II) are either known compounds or are available by conventional procedures, e.g. as follows:

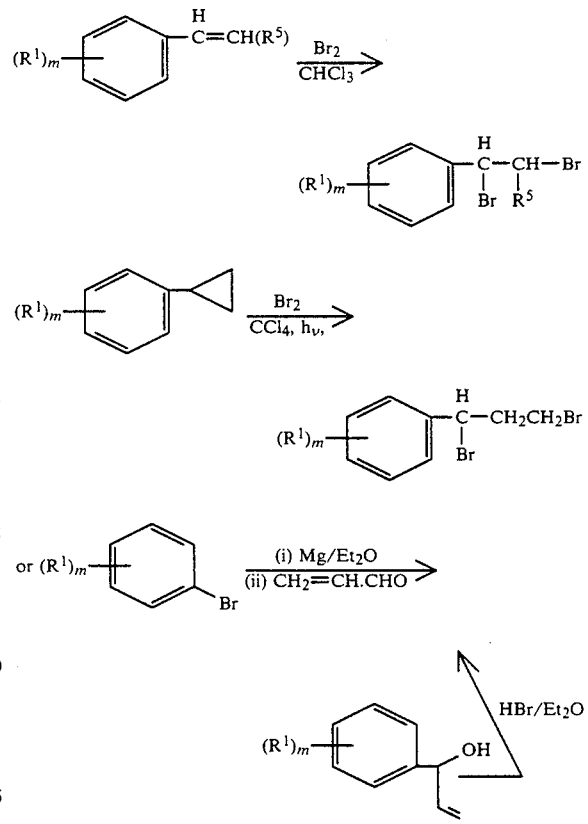

The reaction of the arylcyclopropane with bromine is described in *J. Org. Chem.*, 37(8), 1094 (1972). For the reaction of the aryl bromide with Mg etc., see *J. Amer. Chem. Soc.*, 1968, 90, 1623.

The styrene starting materials are either known compounds or can be prepared conventionally, e.g. from the appropriate benzaldehyde via a Wittig reaction (see Organic Reactions, 14, 290), or from the appropriate aryl halide and ethylene employing the Heck reaction (see *J. Org. Chem.*, 1978, 43, 2454).

In a typical procedure, the dihalo compound (II) and the heterocycle (III) are stirred together at room temperature for up to about 48 hours in a dipolar aprotic solvent capable of solubilizing the heterocycle, e.g. dimethylsulphoxide. This reaction is believed to proceed via the intermediate (IV). If necessary, the reaction can be heated at up to 60° C. to accelerate it. A base, preferably a tertiary amine base such as triethylamine, is then added dropwise, and the resulting mixture is stirred at room temperature for up to about 48 hours. The product (I) can then be isolated and purified by conventional procedures. If desired, the product can be isolated as an acid addition salt which can be obtained by conventional means, e.g. by using hydrogen chloride in ethanol.

The following Examples illustrate the preparation of compounds of the formula (I):

EXAMPLE 1

Preparation of 2-(2,3-Dimethylphenyl)-2,3,5,6-tetrahydroimidazo[2,1-b]thiazole hydrochloride hydrate

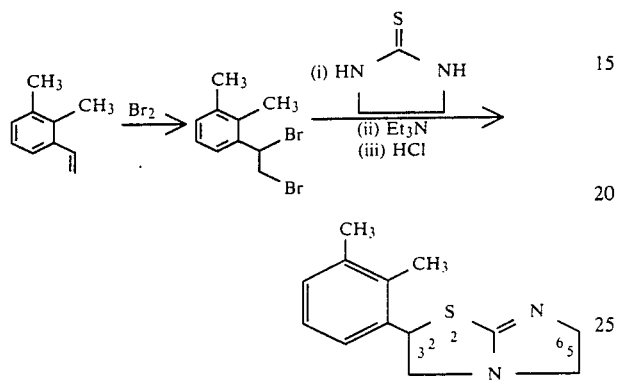

A. To a solution of 2,3-dimethylstyrene (0.67 g, 0.00508M) in chloroform (10 mls) at room temperature, bromine (0.82 g, 0.0051M) was added dropwise. The resulting red solution was stirred for 30 minutes and then decolourised with aqueous sodium metabisulphite solution. The organic phase was separated, dried (MgSO$_4$), and evaporated under reduced pressure.

B. The resulting oil (1 g) was taken up in dry dimethylsulfoxide (5 mls) and ethylene thiourea (0.35 g, 0.0035M) was added. The mixture was stirred at room temperature for 48 hours. Triethylamine (0.35 g, 0.0024M) was added dropwise and the mixture stirred at room temperature for one hour then diluted with water (30 mls), acidified with 2N hydrochloric acid and extracted with ether (10 mls×3). The clear aqueous phase was basified with 2N sodium hydroxide and extracted with ether (70 ml×3). The combined organic layers were dried (MgSO$_4$) and evaporated under reduced pressure. The resulting gum was taken up in ethyl acetate (20 mls) and the solution was stirred whilst a saturated solution of hydrogen chloride in ethanol was added dropwise until no further precipitation occurred. The precipitate was filtered off, washed with ethyl acetate (10 ml), then ether (10 mls) and dried to yield the pure title compound, m.p. 185° C.

Analysis %: Found: C,54.53; H,6.40; N,9.87; $C_{13}H_{16}N_2S.HCl.H_2O$ requires: C,54.44; H,6.68; N,9.77.

The compounds in the following Examples 2–60 were prepared similarly to Example 1B, starting from the appropriate compound of the formula (II) where "Hal" is Br, ethylene thiourea and triethylamine, and were isolated in the form indicated. The product of Example 61 was prepared from styrene, bromine,

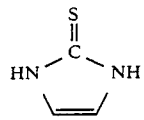

and triethylamine.

Apart from Examples 12 and 59, the starting materials of the formula (II) were always prepared by the bromination of the appropriate styrene similarly to the procedure of Example 1(A). In Example 12, the 1,3-dibromo-1-phenylpropane was prepared by the reaction of bromine with phenylcyclopropane in a conventional manner. In Example 59, the 1,3-dibromo-1-(2,3-dimethylphenyl)propane was prepared from 2,3-dimethylbromobenzene using (i) Mg/Et$_2$O (ii) CH$_2$=CH.CHO and (iii) HBr/Et$_2$O in a conventional manner.

Examples 2-60

| Example No. | (R¹)ₘ | Y | m.p. (°C.) | C | H | N |
|---|---|---|---|---|---|---|
| 2 | H | CH₂ | 169–171* | 54.83 (54.87) | 5.62 5.44 | 12.22 11.84 |
| 3 | 4-chloro | CH₂ | 179–180* | | 3.5–4.6 (m, 6H), 5.84 (t, J8Hz, 1H), 7.3–7.8 (m, 4H), 11.25 (broad s, 1H) | |
| 4 | 4-methyl | CH₂ | 165–166* | 55.79 (56.57) | 5.87 5.93 | 11.17 10.99 |
| 5 | 4-methoxy | CH₂ | 194–195* | 53.17 (53.22) | 5.70 5.58 | 10.46 10.35 |
| 6 | 2-methyl | CH₂ | 195–196* | 56.36 (56.57) | 5.90 5.93 | 11.14 11.00 |
| 7 | 2,4-dimethyl | CH₂ | 189–190* | 57.64 (58.09) | 6.35 6.37 | 10.42 10.42 |
| 8 | 2,5-dimethyl | CH₂ | 189–190* | 57.98 (58.09) | 6.32 6.37 | 10.56 10.42 |
| 9 | 2,6-dimethyl | CH₂ | 121–122 | 66.81 | 6.90 6.94 | 11.90 12.06 |
| 10 | 3-methyl | CH₂ | 112–113** | 54.50 (67.20) | 5.27 5.23 | 9.35 9.08 |
| 11 | 2-bromo | CH₂ | 205–206* | 41.43 (41.33) | 3.68 3.78 | 9.16 8.76 |
| 12 | H | (CH₂)₂ | 129–130 | 65.56 (66.02) | 6.35 6.46 | 12.82 12.83 |
| 13 | H | Trans-CH(CH₃)— | 73–74 | | 1.1 (d,J7Hz,3H), 2.4–3.7 (m,4H), 3.8–4.3 (m,2H), 4.8(d,J9Hz,1H), 7.1–7.6 (m,5H) | |
| 14 | 2,3,6-trimethyl | CH₂ | 203–5*** | 60.26 (60.26) | 6.38 6.26 | 6.62 6.69 |
| 15 | 2,3,5,6-tetramethyl | CH₂ | 216–7* | 61.52 (60.69) | 7.14 7.13 | 9.87 9.44 |
| 16 | 2,4,6-trimethyl | CH₂ | 196–197*ᶦ | 57.49 (57.61) | 6.77 6.91 | 9.67 9.60 |
| 17 | 2-fluoro | CH₂ | 206–209* | 51.36 (51.06) | 4.60 4.67 | 11.15 10.83 |
| 18 | 2-chloro | CH₂ | 216–217* | 48.78 (48.00) | 4.27 4.40 | 10.37 10.18 |
| 20 | 2-methyl-3-chloro | CH₂ | 221–2* | 49.51 (49.82) | 4.83 4.88 | 10.02 9.69 |
| 21 | 4-phenoxy | CH₂ | 126° | 3.0–3.8 3.9–4.3 5.16 6.7–7.7 | 4H 2H 1H 9H | (m,CH₂) (m,CH₂) (dd,CH) (m,Ar—H) |
| 22 | 4-phenyl | CH₂ | Gum | 3.0–3.8 3.9–4.3 | 4H 2H | (m,CH₂) (m,CH₂) |

Examples 2-60-continued

| Example No. | (R¹)$_m$ | Y | m.p. (°C.) | C | H | N |
|---|---|---|---|---|---|---|
| | | | | | | Analysis % (or n.m.r.) (Theoretical in brackets) |
| 23 | 2-methoxy | CH$_2$ | 70-72 | 5.25<br>7.2-7.7<br>3.0-4.8<br>4.9<br>5.6<br>6.7-7.7 | 1H<br>9H<br>6H<br>3H<br>1H<br>4H | (dd,CH)<br>(m,Ar—H)<br>(m,CH$_2$)<br>(s,CH$_3$)<br>(t,CH)<br>(m,Ar—H) |
| 24 | 2-trifluoromethyl | CH$_2$ | 200-201* | 46.74<br>(46.68 | 3.88<br>3.92 | 9.11<br>9.07) |
| 25 | 4-fluoro-2-methyl | CH$_2$ | 76-79 | 61.38<br>(60.99 | 5.68<br>5.55 | 11.83<br>11.85) |
| 26 | —(CH$_2$)$_4$— linking the 2 and 3 positions | CH$_2$ | 97 | 61.05<br>(61.10 | 6.07<br>6.49 | 9.44<br>9.50) |
| 27 | —(CH$_2$)$_3$— linking the 2 and 3 positions | CH$_2$ | Gum | 2.1<br>2.8-3.7<br>4.15<br>5.35<br>7.2 | 2H<br>8H<br>2H<br>1H<br>3H | (m,CH$_2$)<br>(m,4 × CH$_2$)<br>(m,CH$_2$)<br>(m,CH)<br>(m,Ar—H) |
| 28 | —CH═CH—CH═CH— linking the 2 and 3 positions | CH$_2$ | 117-118 | 70.53<br>(70.87 | 5.64<br>5.51 | 11.27<br>11.02) |
| 29 | 2-methyl-3-methoxy | CH$_2$ | Gum | 62.61<br>(62.87 | 6.61<br>6.49 | 11.14<br>11.28) |
| 30 | 2-methyl-3-ethyl | CH$_2$ | 162-163** | 56.88<br>(62.87 | 6.04<br>6.27 | 8.34<br>8.30) |
| 31 | 2-methyl-3-bromo | CH$_2$ | 99-101 | 48.45<br>(48.49 | 4.41<br>4.41 | 9.24<br>9.43) |
| 32 | 2-methyl-3-methylthio | CH$_2$ | Gum* | 2.3 3H<br>2.39 3H<br>3.5-4.4<br>5.9 1H | (s,CH$_3$)<br>(s,CH$_3$)<br>6H (m,CH$_2$)<br>(m,CH) | 6.9-7.9 (m,Ar—H) |
| 33 | 2-methyl-3-triflouromethyl | CH$_2$ | Gum | 54.11<br>(54.54 | 4.57<br>4.54 | 9.74<br>9.79) |
| 34 | 2-methyl-3-hydroxymethyl | CH$_2$ | 162-164 | 62.48<br>(62.87 | 6.72<br>6.49 | 10.99<br>11.28) |
| 35 | 2-methyl-3-formyl | CH$_2$ | Gum | 2.7<br>3.1-3.8<br>4.2<br>5.5<br>7.3-8<br>10.4 | 3H<br>4H<br>2H<br>1H<br>3H<br>1H | (s,CH$_3$)<br>(m,3 × CH$_2$)<br>(m,CH$_2$)<br>(t,CH)<br>(m,Ar—H)<br>(s,CHO) |
| 36 | 2-methyl-methoxycarbonyl | CH$_2$ | Gum | 61.02<br>(60.85 | 5.89<br>5.84 | 9.61<br>10.14) |
| 37 | 2-methyl-3-carbamoyl | CH$_2$ | 171-173 | 2.22 3H (s,CH$_3$)<br>3.0-3.8 6H (m,CH$_2$ + NH$_2$)<br>3.84-4.15 2H (m,CH$_2$)<br>5.6 1H (6.J 7Hz,CH) | 6.7-7.2 | 3H (m,Ar—H) |
| 38 | 2-methyl-3-cyano | CH$_2$ | 102.5-103.5 | 63.83<br>(64.17 | 5.98<br>5.39 | 17.34<br>17.27) |
| 39 | 2-methyl-3-methoxymethyl | CH$_2$ | Gum | 2.35<br>3.38<br>4.4 | 3H<br>7H<br>2H | (s,CH$_3$)<br>(s,OCH$_3$,m,2 × CH$_2$)<br>(s,CH$_2$) |

Examples 2-60-continued

| Example No. | $(R^1)_m$ | Y | m.p. (°C.) | | | | Analysis % (or n.m.r.) (Theoretical in brackets) | | |
|---|---|---|---|---|---|---|---|---|---|
| | | | | | | C | | H | N |
| 40 | 2-methyl-3-carboxy | CH$_2$ | 253-4*ϕ | 5.5<br>7-7.7<br>2.5<br>3.6-4.4<br>6.0<br>7.1-7.8 | 1H<br>3H<br>3H<br>8H<br>1H<br>3H | | 1H<br>3H<br>3H<br>8H<br>1H<br>3H | | (m,CH)<br>(m,ArH)<br>(s,CH$_3$)<br>(m)<br>(t,CH)<br>(m,ZrH) |
| 41 | 2-methyl-3-acetamido | CH$_2$ | 150-153 | 2.13<br>2.19<br>3.1-3.7<br>3.9-4.3 | 3H<br>3H<br>4H<br>2H | (s,CH$_3$)<br>(s,CH$_3$)<br>(m,CH$_2$)<br>(m,CH$_2$) | 5.4<br>7.0-7.5<br>8.7 | | 1H (m,CH)<br>3H (m,ArH)<br>1H (broad s,NH) |
| 42 | 2-methyl-3-amino | CH$_2$ | 250-255ƒ+<br>(decomp.) | | | 45.60<br>(45.71) | 5.65<br>5.71 | | 13.34<br>13.33 |
| 43 | 2-methyl-3-hydroxy | CH$_2$ | ~190<br>(decomp.) | 2.2<br>2.0-2.8<br>2.82-3.19<br>5.6 | 3H<br>4H<br>2H<br>1H | (s,CH$_3$)<br>(m,CH$_2$)<br>(m,CH$_2$)<br>(t, J 7Hz,CH) | 6.6-7.2<br>9.0-10 | | 3H (m,Ar—H)<br>1H (broad s,OH) |
| 44 | 3-methoxy | CH$_2$ | 79-81ϕ | | | 57.06<br>(57.12) | 5.90<br>5.59 | | 11.14<br>11.10 |
| 45 | 3-nitro | CH$_2$ | 118-20 | 3.2-3.9<br>4.25<br>5.4 | 4H<br>2H<br>1H | (m,CH$_2$)<br>(t,CH$_2$)<br>(t,CH) | 7.4-8.5 | | 4H (m,ArH) |
| 46 | 3-fluoro | CH$_2$ | 166-167* | 3.7-4.6<br>4.7<br>5.8 | 4H<br>2H<br>1H | (m,CH$_2$)<br>(s,CH$_3$)<br>(t,CH) | 6.9-7.5 | | 4H (m,ArH) |
| 47 | 2-chloro-3-methyl | CH$_2$ | 228-229* | 2.4<br>3.9-4.4<br>6.2<br>7.2-7.7 | 3H<br>6H<br>1H<br>3H | (s,CH$_3$)<br>(m,CH$_2$)<br>(t,CH)<br>(m,Ar—H) | | | |
| 48 | 2-bromo-3-methyl | CH$_2$ | 114-115 | | | 48.96<br>(48.48) | 4.43<br>4.38 | | 9.82<br>9.43) |
| 49 | 2-Iodo-3-methyl | CH$_2$ | 165-166 | | | 41.97<br>(41.87) | 3.63<br>3.81 | | 8.25<br>8.14) |
| 50 | 2,3-dimethyl-4-fluoro | CH$_2$ | 227 Δ<br>(decomp.) | 2.16<br>2.26<br>3.6-4.4<br>4.62 | 3H<br>3H<br>6H<br>2H | (d,m-CH$_3$)6.0<br>(s,o-CH$_3$)<br>(m,CH$_2$)<br>(broad s, H$_2$O) | 1H (t,CH)<br>6.9-7.6 | | 2H (m,Ar—H) |
| 51 | 2,3-dichloro | CH$_2$ | 253-* | | | 42.53<br>(42.65) | 3.68<br>3.55 | | 9.16<br>9.05) |
| 52 | 2-trifluoromethyl-3-methyl | CH$_2$ | Gum | | | 54.18<br>(54.54) | 4.77<br>4.54 | | 10.12<br>9.79) |
| 53 | 2-cyano-3-methyl | CH$_2$ | 159-160 | | | 64.14<br>(64.17) | 5.57<br>5.39 | | 17.24<br>17.27) |
| 54 | 2,6-dichloro | CH$_2$ | gum | 2.8-3.8<br>3.9-4.3<br>6.22<br>6.9-7.35 | 4H<br>2H<br>1H<br>3H | (m,CH$_2$)<br>(m,CH$_2$)<br>(t,CH)<br>(m,ArH) | | | |
| 55 | 3-phenoxy | CH$_2$ | 101-103 | | | 68.80<br>(68.99) | 5.48<br>5.44 | | 9.17<br>9.45) |
| 56 | 2-methyl-3-N,N—dimethylsulphamoyl | CH$_2$ | 101-103 | 2.63<br>2.8 | 3H<br>6H | (s,CH$_3$)<br>(s,2 × CH$_3$) | 5.52<br>7.15-7.5 | | 1H (t,CH)<br>1H (ArH) |

Examples 2-60-continued

| Example No. | (R¹)ₘ | Y | m.p. (°C.) | | | Analysis % (or n.m.r.) (Theoretical in brackets) | | |
|---|---|---|---|---|---|---|---|---|
| | | | | | | C | H | N |
| 57 | 2-hydroxymethyl | CH₂ | 150-151 | 3.0-3.8 | 4H | (m,CH₂) | 7.7-8.1 | 2H (Ar—H) |
| | | | | 3.9-4.4 | 2H | (m,CH₂) | | |
| | | | | 2.85-4.1 | 7H | (m,CH₂ + OH) | | |
| | | | | 4.55 | 2H | (m,CH₂) | | |
| | | | | 5.5 | 1H | (dd, CH) | | |
| | | | | 7.05-7.7 | 4H | (m,Ar—H) | | |
| 58 | 2-methoxy-3-methyl | CH₂ | gum | 2.32 | 3H | (s,CH₃) | 5.64 | 1H (dd,CH) |
| | | | | 2.95-3.7 | 4H | (m,CH₂) | 6.95-7.6 | 3H (m,Ar—H) |
| | | | | 3.76 | 3H | (s,CH₃) | | |
| | | | | 3.96-4.3 | 2H | (m,CH₂) | | |
| 59 | 2,3-dimethyl | (CH₂)₂ $ | 268-269 | | | 51.55 | 5.97 | 8.64 |
| | | | | | | (51.39 | 5.85 | 8.56) |
| 60 | 2-ethoxy | CH₂ | 175-177* | | | 54.76 | 5.70 | 10.02 |
| | | | | | | (54.82 | 6.02 | 9.84) |

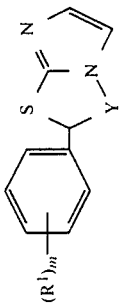

(R¹)ₘ

| 1 | H | CH₂ | 84-85 | | | 64.84 | 4.94 | 14.18 |
| | | | | | | (65.31 | 4.98 | 13.85) |

*hydrochloride salt; ªas oxalate salt; ***as tosylate salt; ᶠas hemihydrate; ᵍas dihydrochloride; ˢhydrobromide; ᵇas monohydrate; and ᐃ as monohydrochloride monohydrate.

EXAMPLE 62

This illustrates an emulsifiable concentrate containing the compound of Example 1. It is prepared by the thorough mixing of the ingredients.

| Constituent | % w/w |
| --- | --- |
| Product of Example 1 | 12.5 |
| "Arylan CA" (Trade Mark, p-dodecylbenzene-sulfonate, anionic surfactant) | 4.0 |
| "Ethylan BV" (Trade Mark, non-ionic surfactant) | 12.0 |
| "Solvesso 200" (Trade Mark, mixture of methyl napthalenes) | 71.5 |

The concentrate is mixed with water to provide an animal dip bath of the required concentration.

As stated previously, the styrenes employed in the preparation of the starting materials (II) are either commercially available or are reported in the literature, or can be prepared conventionally either from the appropriate benzaldehyde via a Wittig reaction (see Organic Reactions, 14, 290), or from the appropriate aryl halide and ethylene employing the Heck reaction (see *J. Org. Chem.*, 1978, 43, 2454). Two representative preparations are described below.

PREPARATION 1

(Witting reaction)

Methyltriphenylphosphonium bromide (6.9 g, 0.019M) was suspended in dry tetrahydrofuran (100 ml) at −40° C. under an atmosphere of dry nitrogen. n-Butyllithium (13.5 ml. of a 1.55M solution in hexane, 0.021M) was added dropwise during 10 minutes and the mixture was stirred at −40° C. for 30 minutes. 3-Chloro-2-methylbenzaldehyde (3.0 g, 0.019M) in dry tetrahydrofuran (10 mls) was then added. The mixture was maintained at −40° C. for 30 minutes and then allowed to warm to room temperature. Hexane (150 ml) was added and the mixture was filtered. The hexane was evaporated to give crude 3-chloro-2-methylstyrene which was used directly without further purification.

PREPARATION 2

(Heck reaction)

2-Bromo-6-trifluoromethyltoluene (2.39 g, 0.01M), palladous acetate (40 mg), tri-ortho-tolylphosphine (120 mg), acetonitrile (5 ml) and triethylamine (5 ml) were placed in a pressure vessel equipped with a magnetic stirred. The sealed vessel was charged with ethylene to give a pressure of 180 p.s.i. and the vessel was heated to 125° C. After 18 hours at 125° C., the vessel was cooled to room temperature and the excess ethylene was vented. The reaction mixture was then poured into ether (50 ml)/petroleum ether (50 ml), and the solid by-products were removed by filtration. Evaporation of the filtrate gave crude 2-methyl-3-trifluoromethylstyrene (2 g) which was used directly without further purification.

The compounds of the formulae (I) and (IA) are particularly useful as acaricides. Using the first Boophilus test method described in the text, the following results were obtained.

| Product of Example No. | Adult Boophilus Dose (μg./δ) | Microplus % Inhibition of Egg Laying |
| --- | --- | --- |
| 1 | 10 | 100 |
| 2 | 10 | 98 |
| 3 | 50 | 100 |
| 5 | 50 | 80 |
| 6 | 10 | 100 |
| 8 | 50 | 100 |
| 9 | 4 | 95 |
| 10 | 50 | 98 |
| 11 | 50 | 70 |
| 12 | 50 | 20 |
| 14 | 50 | 95 |
| 15 | 50 | 20 |
| 16 | 50 | 100 |
| 17 | 50 | 100 |
| 18 | 50 | 95 |
| 19 | 50 | 95 |
| 20 | 50 | 100 |
| 22 | 50 | 60 |
| 23 | 50 | 90 |
| 24 | 50 | 95 |
| 25 | 50 | 95 |
| 26 | 50 | 90 |
| 27 | 50 | 95 |
| 28 | 50 | 20 |
| 29 | 50 | 100 |
| 30 | 50 | 100 |
| 31 | 50 | 95 |
| 32 | 50 | 95 |
| 33 | 50 | 100 |
| 35 | 50 | 10 |
| 38 | 50 | 100 |
| 39 | 50 | 95 |
| 41 | 50 | 95 |
| 42 | 50 | 95 |
| 44 | 50 | 99 |
| 45 | 50 | 95 |
| 46 | 50 | 95 |
| 47 | 50 | 100 |
| 48 | 50 | 100 |
| 49 | 50 | 95 |
| 51 | 50 | 95 |
| 52 | 50 | 100 |
| 53 | 50 | 95 |
| 54 | 50 | 100 |
| 60 | 50 | 70 |

The following activities were recorded against *Lucilia cuprina* larvae, using the test method described in the text:

| Product of Example No. | Dose (mg/m²) | % Kill |
| --- | --- | --- |
| 1 | 100 | 100 |
| 8 | 100 | 41 |
| 20 | 100 | 100 |
| 49 | 100 | 70 |

The following activities were recorded against *Caenorhabditis Elegans* worms using the test method referred to in the text:

| Product of Example No. | Dose (mg/ml) | Result of Dose |
| --- | --- | --- |
| 1 | 0.05 | Inhibits reproduction, 80% kill. |
| 3 | 0.05 | Causes lethargy. |
| 4 | 0.05 | Inhibits reproduction, 30% kill. |
| 5 | 0.05 | Inhibits reproduction. |
| 7 | 0.05 | Causes paralysis and lethargy. |
| 10 | 0.05 | Causes lethargy. |
| 14 | 0.05 | Causes lethargy. |

-continued

| Product of Example No. | Dose (mg/ml) | Result of Dose |
| --- | --- | --- |
| 15 | 0.05 | Causes lethargy. |
| 16 | 0.05 | Causes lethargy. |
| 20 | 0.05 | Causes lethargy and inhibits reproduction. |
| 21 | 0.05 | Causes paralysis. |
| 22 | 0.05 | Causes paralysis and lethargy, inhibits reproduction, 95% kill. |
| 25 | 0.05 | Causes paralysis and lethargy. |
| 30 | 0.01 | Causes paralysis. |
| 31 | 0.05 | Causes paralysis and lethargy, inhibits reproduction, 40% kill. |
| 33 | 0.05 | Causes paralysis and lethargy, inhibits reproduction, 50% kill. |
| 36 | 0.05 | Causes paralysis and lethargy. |
| 48 | 0.05 | Causes lethargy and inhibits reproduction, 5% kill. |
| 61 | 0.05 | Causes lethargy and inhibits reproduction, 40% kill. |

I claim:

1. A compound of the formula:

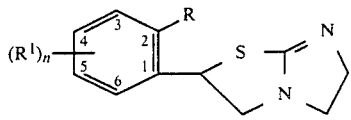

and the non-toxic acid addition salts thereof, wherein $(R^1)_n$ is located at the 3- or 6-position of the benzene ring and n is 1, and R and $R^1$ are each methyl.

2. A compound as claimed in claim 1 wherein $(R^1)_n$ is at the 3-position of the benzene ring.

3. A compound as claimed in claim 1 wherein $(R^1)_n$ is at the 6-position of the benzene ring.

4. A method of combatting ectoparasite infestations in an animal, which comprises administering to said animal an ectoparasiticidal-effective amount of a compound selected from the group consisting of bicyclic imidazole or imidazoline bases of the formula:

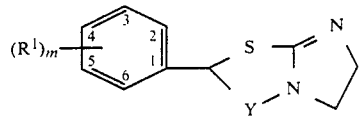

and the non-toxic acid addition salts thereof, wherein $(R^1)_m$ represents up to four optional substituents, m being zero or an integer of from 1 to 4, and each $R^1$ is independently selected from the group consisting of $C_1$-$C_4$ alkyl, $C_1$-$C_4$ alkoxy, $C_1$-$C_4$ alkylthio, halogen, trifluoromethyl, nitro, cyano, phenyl, phenoxy, —$NH_2$, —$NHCOCH_3$, —OH, —$CH_2OH$, —$CH_2OCH_3$, —CHO, —COOH, —COO($C_1$-$C_4$ alkyl), —$CONH_2$ and —$SO_2N(C_1$-$C_4$ alkyl$)_2$; or $R^1$ and $R^1$, when taken together, represent a —CH=CH—CH=CH—, —$(CH_2)_3$— or —$(CH_2)_4$— group attached to adjacent positions of the benzene ring; and Y is —$(CH_2)_2$— or —$CHR^2$—, with $R^2$ being hydrogen or methyl; and the dashed line represents an optional bond.

5. The method as claimed in claim 1 wherein the compound administered is 2-(2,3-dimethylphenyl)-2,3,5,6-tetrahydroimidazo[2,1-b]thiazole.

6. The method as claimed in claim 1 wherein the compound administered is 2-(2,6-dimethylphenyl)-2,3,5,6-tetrahydroimidazo[2,1-b]thiazole.

7. The method as claimed in claim 1 wherein the compound administered is 2-(2-methyl-3-chlorophenyl)-2,3,5,6-tetrahydroimidazo[2,1-b]thiazole.

8. The method as claimed in claim 1 wherein the compound administered is 2-(2-methyl-3-bromophenyl)-2,3,5,6-tetrahydroimidazo[2,1-b]thiazole.

9. The method as claimed in claim 1 wherein the compound administered is 2-(2-methyl-3-trifluoromethylphenyl)-2,3,5,6-tetrahydroimidazo[2,1-b]thiazole.

10. The method as claimed in claim 1 wherein the compound administered is 2-(2-chloro-3-methylphenyl)-2,3,5,6-tetrahydroimidazo[2,1-b]thiazole.

11. The method as claimed in claim 1 wherein the compound administered is 2-(2-bromo-3-methylphenyl)-2,3,5,6-tetrahydroimidazo[2,1-b]thiazole.

12. The method as claimed in claim 1 wherein the compound administered is 2-(2-iodo-3-methylphenyl)-2,3,5,6-tetrahydroimidazo[2,1-b]thiazole.

13. The method as claimed in claim 1 wherein the compound administered is 2-(2-trifluoromethyl-3-methylphenyl)-2,3,5,6-tetrahydroimidazo[2,1-b]thiazole.

14. A composition suitable for administration to an animal comprising a diluent or carrier and a compound of the formula of claim 1 in an amount effective for combatting ectoparasite infestations in said animal.

* * * * *